United States Patent [19]

Masakazu et al.

[11] Patent Number: 4,855,409

[45] Date of Patent: Aug. 8, 1989

[54] NOVEL POLYPEPTIDES AND METHOD OF PRODUCING SAME

[75] Inventors: Kikuchi Masakazu, Toyono; Kurokawa Tsutomu, Kawanishi; Honda Susumu, Takatsuki, all of Japan

[73] Assignee: Takeda Chemical Industries, Ltd., Osaka, Japan

[21] Appl. No.: 129,947

[22] Filed: Nov. 23, 1987

Related U.S. Application Data

[63] Continuation of Ser. No. 685,819, Dec. 14, 1984, abandoned.

[30] Foreign Application Priority Data

Jun. 6, 1984 [WO] World Int. Prop. O. .......... PCT/JP84/00292
Sep. 11, 1984 [WO] World Int. Prop. O. .......... PCT/JP84/00434

[51] Int. Cl.[4] ............................................. A61K 45/02
[52] U.S. Cl. .................................. 530/351; 424/85.5; 435/811
[58] Field of Search ................. 530/350, 351; 424/85; 435/811

[56] References Cited

U.S. PATENT DOCUMENTS 4,604,284  8/1986  Kung et al. ............................ 435/68
4,714,611  12/1987  Yasaburgo et al. .................. 530/351
4,727,138  2/1988  Goeddel et al. ...................... 536/27

FOREIGN PATENT DOCUMENTS 0077670  4/1983  European Pat. Off. .
0103898  3/1984  European Pat. Off. .
0146354  12/1984  European Pat. Off. .
040053   11/1983  World Int. Prop. O. ........... 424/85

OTHER PUBLICATIONS

Tanaka et al, "Expression in *Escherichia coli* of Chemically Synthesized Gene for the Human Immune Interferon", *Nucleic Acids Research*, vol. 11, No. 6, 1983, pp. 1707-1723.
Gray, P. W. et al., Nature, 295, 503-508 (1982).
Devos, R. et al., Nucleic Acids Research, 10, 2487-2501 (1982).
H. M. Johnson et al., J. Immunology, 129, 2357-2359 (1982).
D. J. Capon et al., Conference Abstracts, 3rd Annual International Congress for Interferon Research Miami, Fla., 1982.
Nikkei Biotech., 6-4-84 (No. 65).

*Primary Examiner*—Delbert R. Phillips
*Assistant Examiner*—Nathan M. Nutter
*Attorney, Agent, or Firm*—David G. Conlin; Ronald I. Eisenstein

[57] ABSTRACT

A novel polypeptide which is at least equivalent in biological activity to IFN-γ and is resistant to dimerization and polymerization, a transformant which carries a DNA coding for a novel polypeptide, and a method of producing a novel polypeptide from the culture of the transformant.

The DNA coding for the novel polypeptide can be produced, for example, starting with a known plasmid which contains the IFN-γ gene (cDNA), namely pHITtrp1101 or pHITtrp 1201.

Insertion of this DNA into a vector followed by introduction into a host gives the transformant. An antibody column is used for the purification of the polypeptide from the culture.

The novel polypeptide produced can be used as an antiviral agent or an antitumor agent.

1 Claim, 5 Drawing Sheets

NOVEL POLYPEPTIDES AND METHOD OF PRODUCING SAME

This is a continuation of co-pending application Ser. No. 685,819 filed on Dec. 14, 1984, now abandoned.

TECHNICAL FIELD

This invention relates to novel polypeptides useful as drugs, among others, and a method of producing the same.

BACKGROUND ART

Type γ interferon (hereinafter sometimes abbreviated as IFN-γ) is produced by immunocompetent cells under circumstances such that blastoid transformation of lymphocytes or production of lymphokines takes place and accordingly it is also called immune interferon. IFN-γ is said to have higher antiproliferative or antitumor activity as compared with IFN-α and IFN-β, and therefore it is much expected of from the clinical application viewpoint. However, due to various limitations, such as requirement of fresh lymphocytes for its production, any efficient production systems have not been established yet.

Recently, the recombinant DNA technology has come into wide use and, as a result, a complementary DNA (cDNA) for IFN-γ has been cloned and its nucleotide sequence and the amino acid sequence expected therefrom have been disclosed. It is now possible to express the cDNA or other chemically synthesized genes in a variety of hosts [Gray, P. W. et al., Nature, 295, 503 (1982); Devos, R. et al., Nucleic Acids Res., 10, 2487 (1982); Tanaka, S. et al., Nucleic Acids Res., 11, 1707 (1983); etc.].

Furthermore, the method of purification using monoclonal antibodies has enabled large-scale production of IFN-γ by the recombinant DNA technology (recombinant IFN-γ; hereinafter sometimes referred to as rIFN-γ) [cf. EPC (laid open) No. 0103898], and its clinical use is expected to be near at hand.

However, rIFN-γ thus obtained is unstable, tending to form a dimer or polyner. Therefore, it is difficult to purify it or make it into pharmaceutical preparations. Highly sophisticated techniques are required for its purification and the preparation of dosage forms containing it.

The present inventors considered that the above drawback of the known rIFN-γ might be due to the two Cys residues occurring in the N-terminal portion thereof and, based on this idea, have now succeeded in producing novel polypeptides which are at least equivalent in biological activity to rIFN-γ and resistant to dimerization or polymerization and have thus completed the present invention.

DISCLOSURE OF THE INVENTION

The invention provides polypeptides of the formula (N) H—X—Y—Asp Pro Tyr Val Lys Glu Ala Glu Asn (I)

Leu Lys Lys Tyr Phe Asn Ala Gly His Ser Asp Val

Ala Asp Asn Gly Thr Leu Phe Leu Gly Ile Leu Lys

Asn Trp Lys Glu Glu Ser Asp Arg Lys Ile Met Gln

Ser Gln Ile Val Ser Phe Tyr Phe Lys Leu Phe Lys

Asn Phe Lys Asp Asp Gln Ser Ile Gln Lys Ser Val

Glu Thr Ile Lys Glu Asp Met Asn Val Lys Phe Phe

Asn Ser Asn Lys Lys Lys Arg Asp Asp Phe Glu Lys

Leu Thr Asn Tyr Ser Val Thr Asp Leu Asn Val Gln

Arg Lys Ala Ile His Glu Leu Ile Gln Val Met Ala

Glu Leu Ser Pro Ala Ala Lys Thr Gly—Z—OH (C)

wherein X is Met or a bond, Y is Cys-Gln, Gln, <Gln or a bond, and Z is a peptide or amino acid residue having 1 to 16 amino acids counting from the N terminus of the peptide chain of (N) Lys Arg Lys Arg Ser Gln Met Leu Phe Arg Gly Arg Arg Ala Ser Gln (C), an industrially advantageous method of producing the same and transformants which can be used in producing the same.

Referring to the polypeptides (I), X is preferably a bond. Y is preferably Cys-Gln, Gln or <Gln, in particular <Gln. Z is preferably Lys, Lys-Arg-Lys-Arg-Ser-Gln-Met-Leu-Phe-Arg-Gly-Arg (II) or Lys-Arg-Lys-Arg-Ser-Gln-Met-Leu-Phe-Arg-Gly-Arg-Arg-Ala-Ser-Gln (III).

In particularly preferred polypeptides (I), X is a bond, Y is Cys-Gln or <Gln and Z is Lys or the peptide residue (III).

It is to be noted that, in polypeptides (I), X is a bond when Y is <Gln.

Polypeptides (I) can be produced with advantage, for example, by growing a transformant carrying a DNA having ATG at the 5' terminus, coding region of the polypeptide of the formula (N) H—Y'—Asp Pro Tyr Val Lys Glu Ala Glu Asn (I')

Leu Lys Lys Tyr Phe Asn Ala Gly His Ser Asp Val

Ala Asp Asn Gly Thr Leu Phe Leu Gly Ile Leu Lys

Asn Trp Lys Glu Glu Ser Asp Arg Lys Ile Met Gln

Ser Gln Ile Val Ser Phe Tyr Phe Lys Leu Phe Lys

Asn Phe Lys Asp Asp Gln Ser Ile Gln Lys Ser Val

Glu Thr Ile Lys Glu Asp Met Asn Val Lys Phe Phe

Asn Ser Asn Lys Lys Lys Arg Asp Asp Phe Glu Lys

Leu Thr Asn Tyr Ser Val Thr Asp Leu Asn Val Gln

Arg Lys Ala Ile His Glu Leu Ile Gln Val Met Ala

Glu Leu Ser Pro Ala Ala Lys Thr Gly—Z—OH (C)

wherein Y' is Cys-Gln or a bond and Z is a peptide or amino acid residue having 1 to 16 amino acids counting from the N terminus of the peptide chain of (N) Lys Arg Lys Arg Ser Gln Met Leu Phe Arg Gly Arg Arg Ala Ser Gln (C), downstream from ATG and a translational termination codon subsequent to the coding region.

Referring to the above-mentioned DNA, the region coding for the polypeptide (I') may have any of the base sequences which code for the above polypeptide (I'), such as:

```
(5') Y¹—GAC CCA TAT GTA AAA GAA GCA GAA AAC CTT    (IV)

AAG AAA TAT TTT AAT GCA GGT CAT TCA GAT GTA GCG

GAT AAT GGA ACT CTT TTC TTA GGC ATT TTG AAG AAT

TGG AAA GAG GAG AGT GAC AGA AAA ATA ATG CAG AGC

CAA ATT GTC TCC TTT TAC TTC AAA CTT TTT AAA AAC

TTT AAA GAT GAC CAG AGC ATC CAA AAG AGT GTG GAG

ACC ATC AAG GAA GAC ATG AAT GTC AAG TTT TTC AAT

AGC AAC AAA AAG AAA CGA GAT GAC TTC GAA AAG CTG

ACT AAT TAT TCG GTA ACT GAC TTG AAT GTC CAA CGC

AAA GCA ATA CAT GAA CTC ATC CAA GTG ATG GCT GAA

CTG TCG CCA GCA GCT AAA ACA GGG—Z¹   (3')
``` wherein Y¹ is TGC CAG or CAG or a bond and Z¹ is a base sequence having 1 to 16 codons counting from the 5' terminus of the base sequence (5') AAG CGA AAA AGG AGT CAG ATG CTG TTT CGA GGT CGA AGA GCA TCC CAG (3′). Particularly preferred are those cases in which $Y^1$ is TGC CAG or CAG and $Z^1$ is AAG CGA AAA AGG AGT CAG ATG CTG TTT CGA GGT CGA AGA GCA TCC CAG (V). As the translation termination codon, there is preferred TAA, TGA or TAG, in particular TAA.

The above DNA may contain, between the ATG at 5′ end and the polypeptide (I′)-encoding DNA, a DNA coding for the signal peptide Lys-Tyr-Thr-Ser-Tyr-Ile-Leu-Ala-Phe-Gln-Leu-Cys-Ile-Val-Leu-Gly-Ser-Leu-Gly, for example AAA TAT ACA AGT TAT ATC TTG GCT TTT CAG CTC TGC ATC GTT TTG GGT TCT CTT GGC.

It is preferred that the above DNA has a promoter upstream from ATG. Said promoter may be any promoter provided that it fits the host to be used in obtaining transformant.

For example, there may be mentioned the trp, lac, rec A, $\lambda P_L$ and lpp promoters for use in *Escherichia coli* (e.g. 294, W3110, DH1), the SPO1, SPO2 and penP promoters for use in *Bacillus subtilis* (e.g. MI, 114), the PHO5, PGK, GAP and ADH promoters for use in *Saccharomyces cerevisiae* (e.g. AH22) and the SV-40-derived promoter for use in animal cells (e.g. monkey COS-7 cells, chinese hamster CHO cells). It is particularly preferred that the trp promoter is used with *Escherichia coli* as the host.

The DNA (plasmid) having ATG at the 5′ end thereof and, downstream therefrom, a region coding for the polypeptide (I′) and then a translation termination codon can be produced by processing a known IFN-γ cDNA synthesized chemically or produced by genetic engineering techniques or a chromosome-derived IFN-γ DNA.

For more detailed explanation of the above production method, a method of producing a plasmid containing a DNA having a region coding for the polypeptide (I′) (Z being the peptide (III) using, as the starting material, the known plasmid pHITtrp1101 containing the IFN-γ gene (cDNA) [cf. Reference Example 2 (iii) of EPC (laid open) No. 0103898] is described below by way of example.

The plasmid pHITtrp1101 is subjected to simultaneous digestion with restriction enzymes, for example AvaII and PstI. This digestion gives a DNA coding for IFN-γ lacking Cys-Tyr-Cys-Gln at the N terminal thereof. Then, a synthetic adapter containing ATG (start codon) and coding for Cys-Gln, a synthetic adapter containing the start codon and coding for Gln or a synthetic adapter containing the start codon, for instance, is synthesized by the phosphotriester method [Crea, R. et al., Proc. Natl. Acad. Sci. USA, 75, 5765 (1978)] and joined to the DNA coding for IFN-γ lacking Cys-Tyr-Cys-Gln. The resulting DNA can be joined to an appropriate promoter, downstream therefrom, and then introduced into an appropriate host. An SD (Shine and Dalgarno) sequence may be inserted downstream from the promoter, as necessary.

The transformant according to the invention can be produced by transforming a host with the expression plasmid obtained in the above manner by the per se known method [Cohen, S. N. et al., Proc. Natl. Acad. Sci. USA, 69, 2110 (1972)].

The polypeptide (I) can be produced by cultivating the above transformant and isolating the polypeptide (I) thus produced and accumulated in the culture.

The medium is, for example, M9 medium containing glucose and casamino acids [Miller, J., Experiments in Molecular Genetics, 431–433 (Cold Spring Harbor Laboratory, New York, 1972)]. An agent such as 3β-indolylacrylic acid may be added to the medium as necessary for increasing the promoter efficiency.

The cultivation is generally conducted at 15°–43° C. for 3 to 24 hours, with aeration and/or stirring as necessary.

When the transformant used carries the λcIts repressor and an expression vector containing the PL promoter, the cultivation is preferably carried out at a relatively low temperature of about 30° C. to 36° C. and the λcIts repressor inactivation at about 37° C. to 42° C. For more effective functioning of the rec A promoter or, in other words, derepressing the repressing function of the rec A gene expression, mitomycin C, nalidixic acid or the like agent may be added or ultraviolet irradiation may be performed, as necessary.

After cultivation, cells are harvested by the known method, suspended, for example, in a buffer and disrupted by treatment with a protein denaturing agent, sonication, or enzymatic treatment with lysozyme or the like, for instance. Centrifugation or the like known separation method then gives a supernatant.

The polypeptide (I) in which Z is a polypeptide comprising not more than 15 amino acids or an amino acid residue can also be produced by cultivating a transformant carrying a DNA which has a region coding for the polypeptide (I') which contains more amino acids than those contained in said Z (for instance, the case in which Z is the whole of the above-defined peptide comprising all the 16 amino acids) and purifying the product polypeptide under conditions such that the product is easily exposed to the action of protease occurring in the transformant.

The polypeptide (I) can be isolated from the supernatant obtained in the above manner by following an ordinary method of protein purification. In particular, the purification can be effected with advantage using an antibody, particularly in the form of an antibody column, which is capable of binding IFN-γ or the polypeptide (I), for example an antibody column comprising a monoclonal antibody against the peptide H-Lys-Arg-Lys-Arg-Ser-Gln-Met-Leu-Phe-Arg-Gly-Arg-Arg-Ala-Ser-Gln-OH [EPC (laid open) No. 0103898, Example 12 (γ2-11.1 monoclonal antibody column) or an antibody column prepared in the same manner using the antibody of Example 18 (γ3-11.1 monoclonal antibody] or an antibody column comprising a monoclonal antibody for the peptide <Gln-Asp-Pro-Tyr-Val-Lys-Glu-Ala-Glu-Asn-Leu-Lys-Lys-Tyr-Phe-Asn-Ala-Gly-OH [Japanese Patent Application No. 215168/1983 (filed Nov. 15, 1983), Example 11 (WNγ2-76.53 monoclonal antibody column)].

In carrying out the purificaiton using the above-mentioned antibody column, a material containing the polypeptide (I) is dissolved, for example, in a nearly neutral buffer, such as a phosphate buffer or a Tris-hydrochloride buffer, and applied to the antibody column for adsorption. The column is washed with the same buffer and then the polypeptide (I) is eluted. As the eluent, there is used a weakly acidic solution (e.g. acetic acid solution), a polyethylene glycol-containing solution, a solution containing a peptide higher in affinity to the antibody than the polypeptide (I), a high concentration salt solution, or a solution prepared by combining these, preferably the one which does not promote decomposition of the polypeptide (I) to a considerable extent.

The column eluate is neutralized with a buffer in the conventional manner. The above antibody column purification procedure can be conducted again as necessary.

When Y in the polypeptide (I) is Cys-Gln, Gln or a bond, it is also possible to recover the polypeptide in which X is a bond and the one in which X is Met together in the form of a mixture.

When the N terminal amino acid of polypeptide (I) is Gln, the peptide may be recovered as a mixture with the polypeptide (I) in which the N terminal amino acid is <Gln, as the case may be. Such mixture also can be used for the purposes mentioned below. In necessary, however, the peptide (I) can be converted to the polypeptide (I) in which the N terminal amino acid is <Gln by heating or treatment with a weak acid (e.g. diluted acetic acid) following the above purification procedure.

The thus-obtained solution of polypeptide (I) is subjected to dialysis and, if desired, can be lyophilized to give a powder. In carrying out the lyophilization, a stabilizer such as sorbitol, mannitol, dextrose, maltose or glycerol can be added.

The thus-obtained polypeptide (I) contains only one Cys or no Cys, so that it can be recovered in the form of a stable monomer which is resistant to dimerization or polymerization as compared with the so-far known rIFN-γ. For instance, it hardly produces a precipitate during the concentrating procedure and the decrease of its biological activity with the lapse of time is very little. Accordingly, it can advantageously be used as a drug, for instance.

The polypeptide (I) according to the invention can be purified to an extent such that the specific activity as determined by antiviral activity measurement in a test for the effect of inhibiting the cytopathic effect of vesicular stomatitis virus (VSV) on human amnion-derived WISH cells amounts to not less than $10^7$ U/mg, and can be used for the same purposes and in the same manner as the known rIFN-γ [Gray, P. W. et al., vide supra] or nature-derived IFN-γ (=type 2 IFN) [Salvin et al., J National Cancer Institute, 55, 1233 (1975)].

The polypeptide (I) according to the invention exhibits antiviral, antitumor, antiproliferative and immunopotentiating activities. The polypeptide (I) of the invention can be mixed with sterile water, human serum albumin (HSA), physiological saline and other known physiologically acceptable carriers and can be administered parenterally or topically. For instance, it can be administered in a dose of $1 \times 10^5$ to $1 \times 10^8$ units, preferably $4 \times 10^6$ to $4 \times 10^7$ units, per human adult, for example by intravenous or intramuscular injection.

A pharmaceutical preparation containing the polypeptide (I) according to the invention may also contain other physiologically acceptable active ingredients such as salt, diluent, adjuvant, other carriers, buffer, binding agent, surfactant and preservative. A parenteral preparation is provided in the form of a solution in sterile water in ampul, a suspension in a physiologically acceptable solvent in ampul, or a sterile powder (generally obtainable by lyophilization of a solution of polypeptide (I) in ampul which is to be diluted at the time of use with a physiologically acceptable liquid diluent.

Furthermore, the pharmaceutical preparation containing the polypeptide (I) according to the invention may contain 1 to 99%, based on the polypeptide (I) according to the invention, of an active ingredient such as IFN-α, IFN-β or IFN-γ or a lymphokine such as interleukin 2.

In the present specification and the accompanying drawings and claims, the amino acids, peptides, protective groups, active groups and so on, when indicated by abbreviations, are indicated by abbreviations adopted by the IUPAC-IUB (Commision on Biological Nomenclature) or in common use in the relevant fields. Examples are given below in Table 1. In case optical isomerism is involved, the amino acids and so on are in the L form unless otherwise specifically indicated.

TABLE 1

| | |
|---|---|
| DNA: | Deoxyribonucleic acid |
| A: | Adenine |
| T: | Thymine |
| G: | Guanine |
| C: | Cytosine |
| RNA: | Ribonucleic acid |
| dATP: | Deoxyadenosine triphosphate |
| dTTP: | Deoxythymidine triphosphate |
| dGTP: | Deoxyguanosine triphosphate |
| dCTP: | Deoxycytidine triphosphate |
| ATP: | Adenosine triphosphate |
| EDTA: | Ethylenediaminetetraacetic acid |
| SDS: | Sodium dodecyl sulfate |
| Gly: | Glycine |
| Ala: | Alanine |
| Val: | Valine |
| Leu: | Leucine |
| Ile: | Isoleucine |
| Ser: | Serine |
| Thr: | Threonine |

TABLE 1-continued

| | |
|---|---|
| Cys: | Cysteine |
| Met: | Methionine |
| Glu: | Glutamic acid |
| Asp: | Aspartic acid |
| Lys: | Lysine |
| Arg: | Arginine |
| His: | Histidine |
| Phe: | Phenylalanine |
| Tyr: | Tyrosine |
| Trp: | Tryptophan |
| Pro: | Proline |
| Asn: | Asparagine |
| Gln: | Glutamine |
| <Gln: | Pyroglutamine |

The antiviral activity (IFN-γ activity) data for polypeptides as described in the present specification in terms of U/ml (units/ml) are those obtained in the following manner. The potency of leukocyte-derived crude IFN-γ was measured, in comparison with international standard IFN-α having an established potency in terms of units, by testing for the activity of inhibiting the cytopathic effect of VSV on the human amnion-derived FL cell line. Based on the potency comparison, the potency of the leukocyte-derived crude IFN-γ was determined and this crude IFN-γ was used as a standard sample of IFN-γ. For determining the polypeptide potency of a sample in question, the sample was assayed in the WISH-VSV system mentioned above always in parallel with the standard IFN-γ and the potency of the sample was calculated from the potency ratio thus obtained.

The transformant *Escherichia coli* 294/pHITtrp1101-d2 disclosed hereinbelow in the examples has been deposited with the Institute for Fermentation, Osaka under the deposit number IFO-14350, and with the Fermentation Research Institute (FRI), Agency of Industrial Science and Technology, Ministry of International Trade and Industry, since June 6, 1984 under the deposit number FERM P-7658.

The transformant *Escherichia coli* 294/pHITtrp1201-d4 also has been deposited with the Institute for Fermentation, Osaka under the deposit number IFO-14365, and with the Fermentation Research Institute, Agency of Industrial Science and Technology, Ministry of International Trade and Industry, since Sept. 4, 1984 under the deposit number FERM P-7828.

BEST MODE FOR CARRYING OUT THE INVENTION

The following examples are further illustrative of the invention. However, they are by no means limitative of the present invention.

EXAMPLE 1

Transformant production (i) The IFN-γ expression plasmid pHITtrp1101 [cf. Reference Example 2 (iii) of EPC (laid open) No. 0103898] was digested with the restriction enzymes AvaII and PstI, and a 1 kb AvaII-PstI DNA fragment containing the IFN-γ gene portion was isolated. To this DNA fragment, at the AvaII cohesive end thereof, there was joined the oligonucleotide adapter

CGATAATGTGCCAG

TATTACACGGTCCTG chemically synthesized by the phosphotriester method mentioned above and containing a protein synthesis start codon, using T4 DNA ligase.

Figure 1:
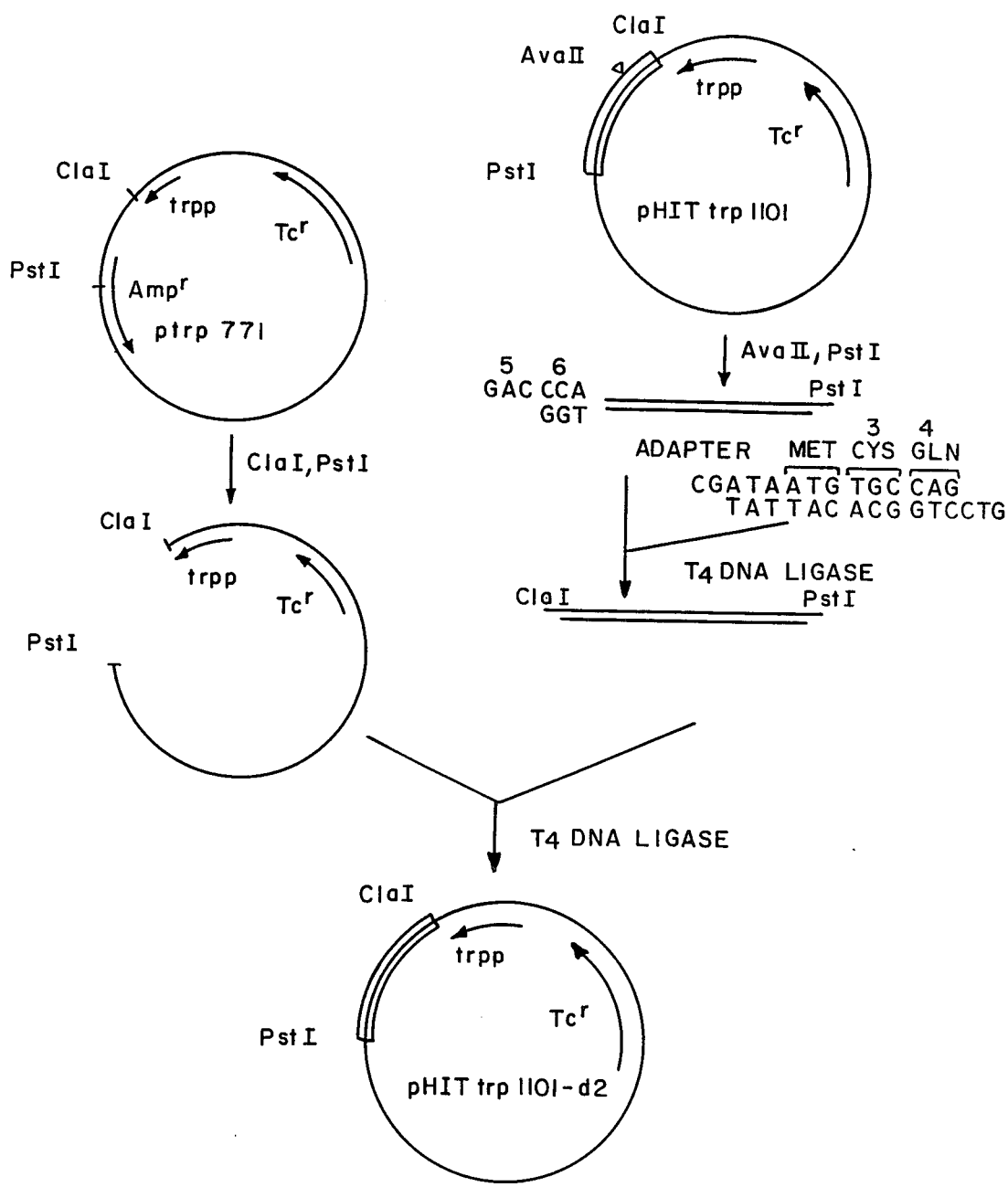
FIG. 1, FIG. 2, FIG. 3, FIG. 4 and FIG. 5 schematically illustrate the processes of constructing the plasmids pHITtrp1101-d2, pHITtrp1201-d3, pHITtrp1201-d4′, pHITtrp1201 and pHIT1201-d4, respectively, which are to be described in Example 1 (i), (ii), (iii) and (iv).

Into a DNA fragment obtained by cutting the plasmid ptrp771 [cf. Reference Example 2 (ii) of the EPC specification just cited above] with the restriction enzymes ClaI and PstI, there was inserted the above-joined IFN-γ gene downstream from the trp promoter. Thus was constructed an expression plasmid, pHITtrp1101-d2, containing the DNA (IV) [$Y^1$ being TGC CAG and $Z^1$ being the base sequence (V)] and coding for the polypeptide (I′) [Y′ being Cys-Gln and Z being the peptide (III)] (cf. FIG. 1).

Transformation of *Escherichia coli* 294 with this plasmid pHITtrp1101-d2 by the method of Cohen et al. (vide supra) gave a transformant, *Escherichia coli* (*E. coli*) 294/pHITtrp 1101-d2, carrying this plasmid.

(ii) In the same manner as Example 1 (i), the IFN-γ expression plasmid pHITtrp1101 was digested with the restriction enzymes AvaII and PstI and a 1 kb AvaII-PstI DNA fragment containing the IFN-γ gene portion was isolated. To this DNA fragment, there was joined the oligonucleotide adapter

AATTCATGCAG

GTACGTCCTG synthesized by the phosphotriester method mentioned above and contaiing a protein synthesis start codon, at the AvaII cohesive end of said fragment using T4 DNA ligase.

Separately, the expression vector ptrp701 [cf. Reference Example 2 (i) of the above-cited EPC specification] was digested with the restriction enzyme EcoRI and then partially digested with ClaI. The resulting cohesive ends were filled in using DNA polymerase I large fragment. The DNA thus obtained was made circular using T4 DNA ligase. In this way, there was constructed an expression vector, ptrp781, with the ClaI recognition site, nearer to the EcoRI recognition site, destroyed and with the EcoRI site available for heterologous gene insertion.

Figure 2:
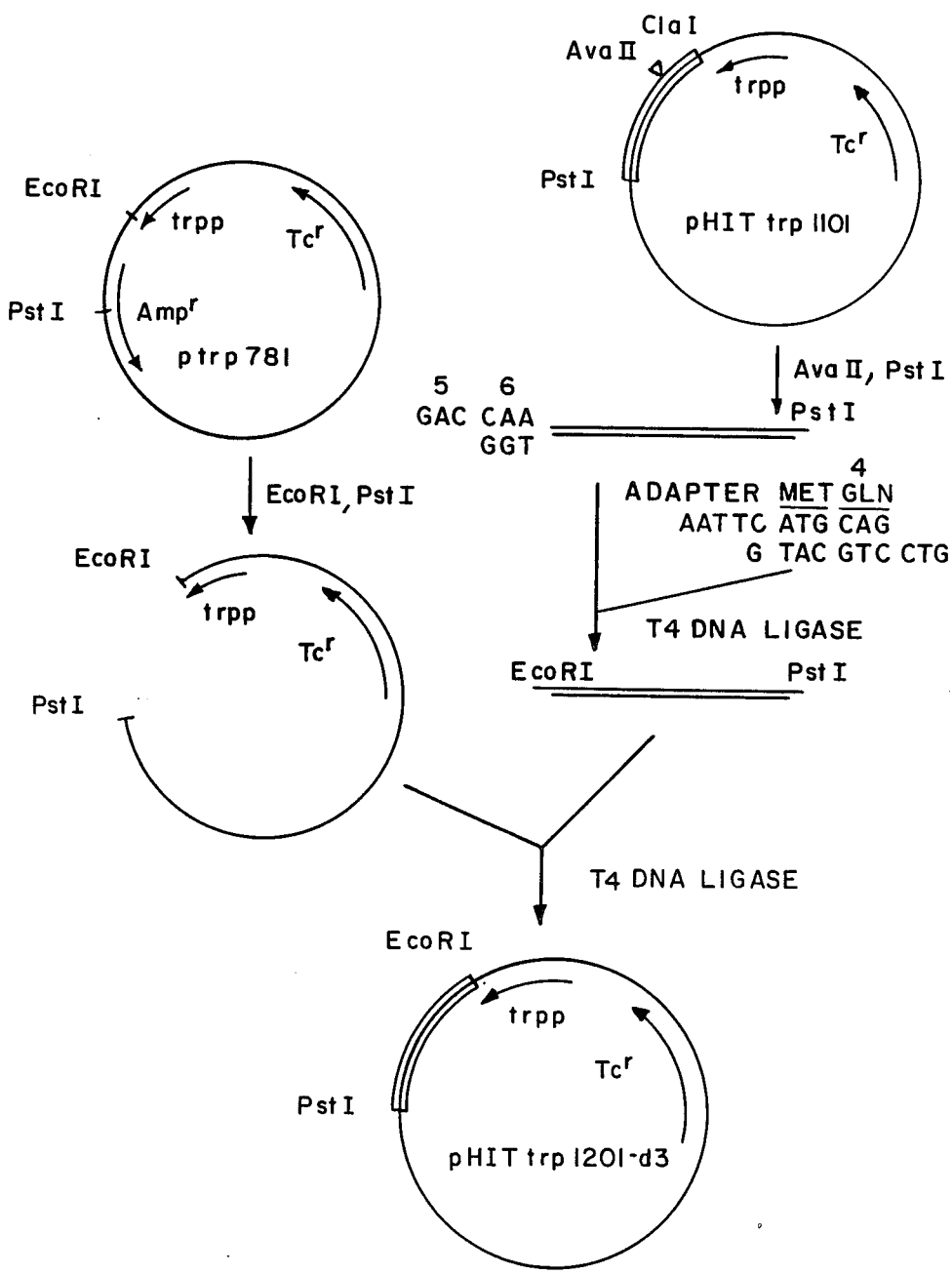

Joining, to a DNA fragment obtained by cutting ptrp781 with the restriction enzymes EcoRI and PstI, the above adapter-joined IFN-γ gene downstream from the tryptophan promoter in the manner of insertion using T4 DNA ligase can lead to construction of an expression plasmid, pHITtrp1201-d3, containing the DNA (IV) [$Y^1$ being CAG and $Z^1$ being the base sequence (V)] and coding for the polypeptide (I′) [Y′ being Gln and Z being the peptide (III)] (cf. FIG. 2). Transformation of *Escherichia coli* 294 with this plasmid pHITtrp1201-d3 by the method of Cohen et al. (vide supra) gives a transformant, *E. coli* 294/pHITtrp1201-d3, carrying said plasmid.

(iii) In the same manner as Example 1 (i), the IFN-γ expression plasmid pHITtrp1101 is digested with the restriction enzymes AvaII and PstI and a 1 kb AvaII-PstI DNA fragment containing the IFN-γ gene portion is isolated. The cohesive end of this DNA fragment as resulting from digestion with the restriction enzyme AvaII is filled in using DNA polymerase I large fragment and the protein synthesis start codon-containing oligonucleotide linker

CATGAATTCATG synthesized chemically is joined to said fragment at said end using T4 DNA ligase.

Figure 3:
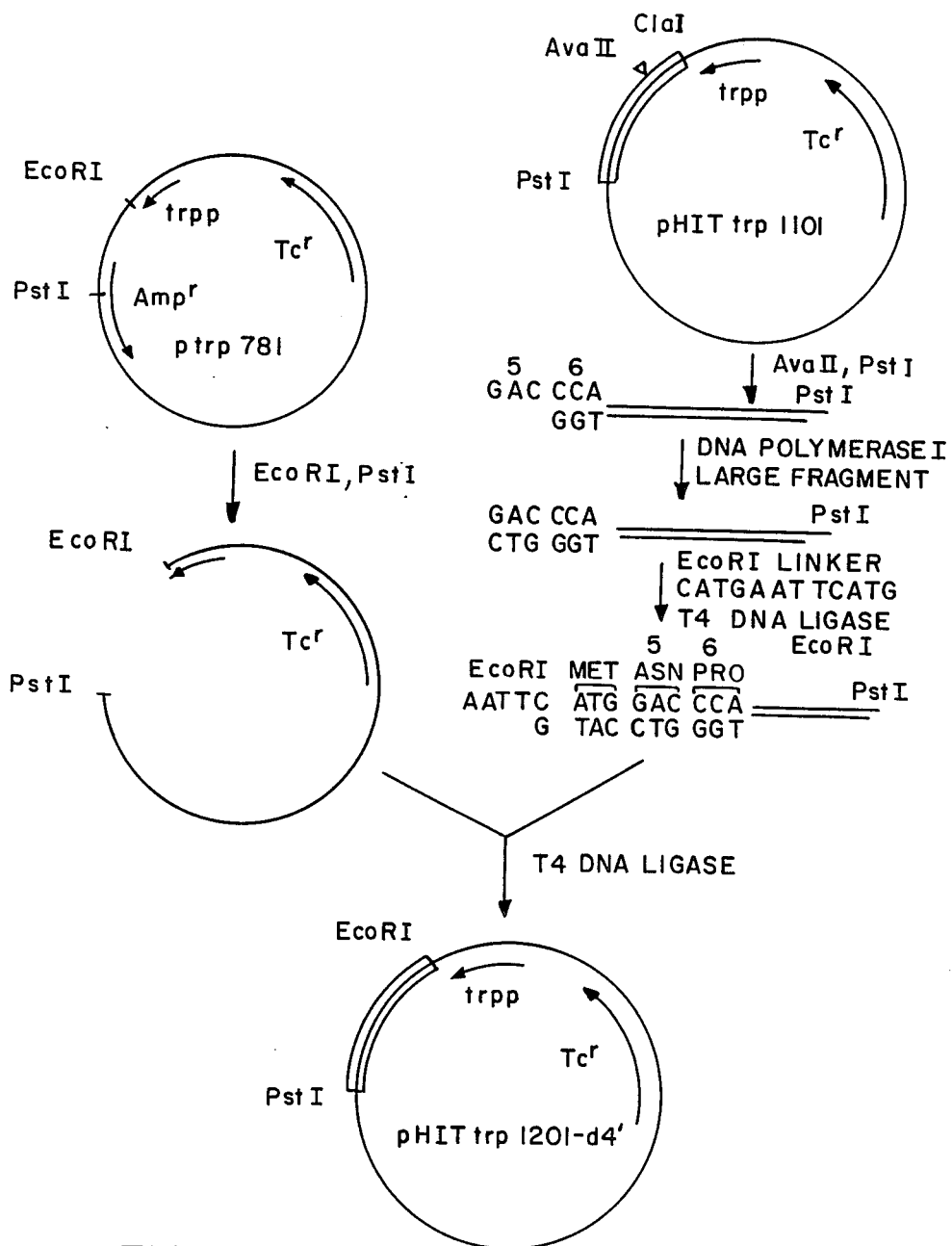

An expression plasmid, pHITtrp1201-d4', containing the DNA (IV) [$Y^1$ being a chemical bonding and $Z^1$ being the base sequence (V)] and coding for the polypeptide (I') [Y' being a chemical bonding and Z being the peptide (III)] can be constructed by digesting the above linker-joined IFN-γ gene with the restriction enzymes EcoRI and PstI followed by inserting into ptrp781 cleaved with the restriction enzymes EcoRI and PstI downstream from the tryptophan promoter (cf. FIG. 3).

Transformation of *Escherichia coli* 294 with this plasmid pHITtrp1201-d4' by the method of Cohen et al. (vide supra) gives a transformant, *E. coli* 294/pHITtrp1201-d4', carrying this plasmid.

(iv) The insert of the IFN-γ gene-containing plasmid pHIT3709 [cf. Reference Example 1 (vii) of EPC (laid open) No. 0103898] was partially digested with the restriction enzyme BstNI. To the thus-obtained BstNI-PstI fragment, at the BstNI cleavage site, there was joined the oligonucleotide adapter

AATTCATGTGTTATTGTC

GTACACAATAACAGT chemically synthesized and containing the protein synthesis start codon ATG, using T4 DNA ligase.

Figure 4:
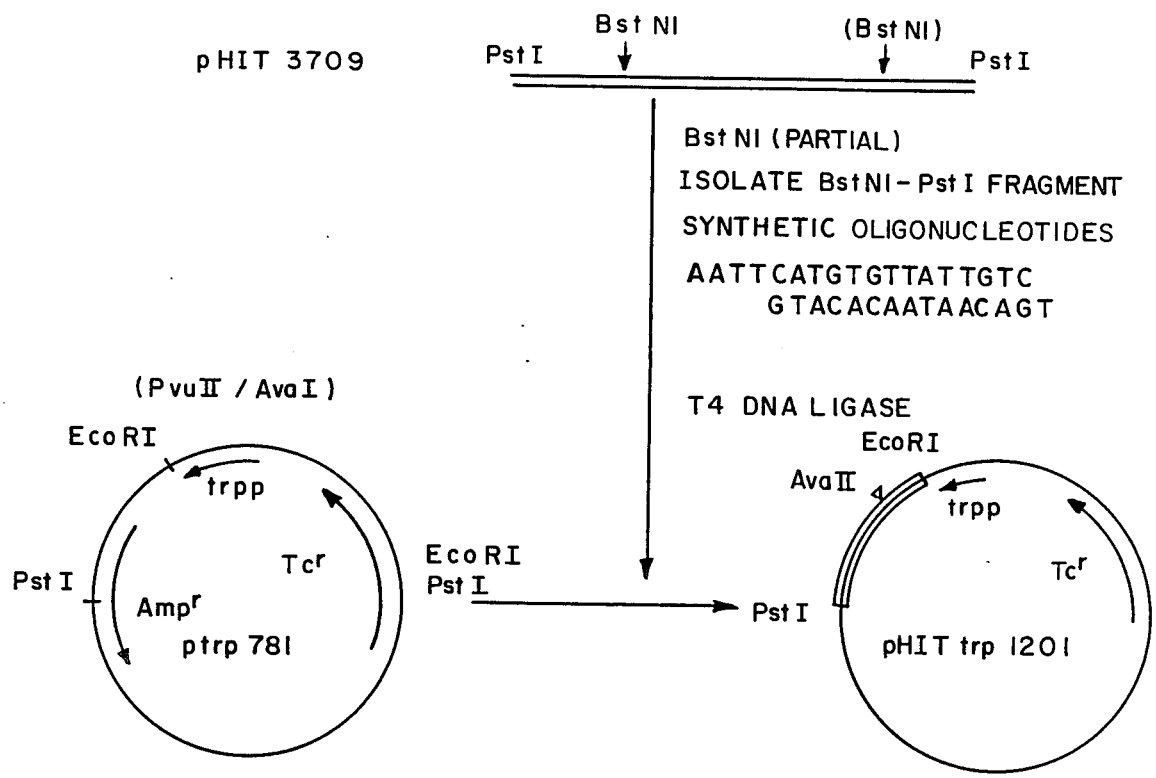

Separately, the above adapter was joined to the plasmid ptrp781 after treatment with EcoRI and PstI, followed by joining of the IFN-γ gene using T4 DNA ligase. There was constructed an INF-γ expression plasmid, pHITtrp 1201 (cf. FIG. 4).

pHITtrp1201 was digested with the restriction enzymes AvaII and PstI and a 1 kb AvaII-PstI DNA fragment containing the IFN-γ gene was isolated.

Figure 5:
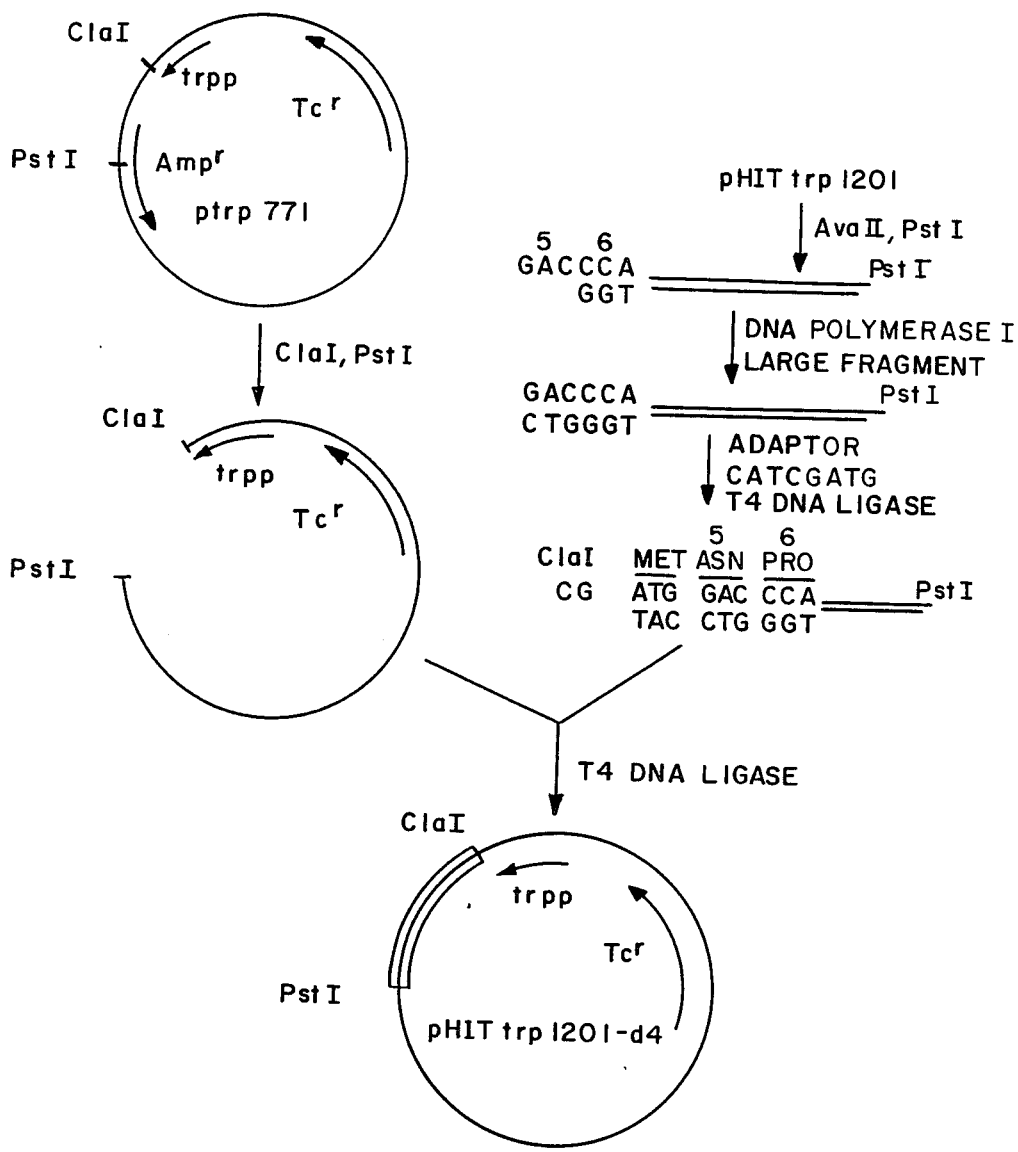

The AvaII cleavage site of this DNA was filled in using DNA polymerase large fragment. To the thus-repaired site, there was joined the protein synthesis start codon-containing oligonucleotide adapter CATCGATG synthesized by the phosphotriester method, using T4 DNA ligase. The IFN-γ gene thus obtained was inserted, downstream from the trp promoter, into the ClaI and PstI-cleaved ptrp771 obtained in Example 1 (i). There was constructed an expression plasmid, pHIT trp1201-d4, coding for the polypeptide (I') [Y' being a chemical bonding and Z being the peptide (III)] (cf. FIG. 5).

Transformation of *E. coli* 294 with this plasmid pHIT trp1201-d4 by the method of Cohen et al. (vide supra) gave a transformant, *E. coli* 294/pHITtrp1201-d4, containing said plasmid.

EXAMPLE 2

Transformant cultivation (i) The strain *E. coli* 294/pHITtrp1101-d2 carrying the plasmid constructed in Example 1 (i) was cultured at 37° C. in M9 medium containing 8 μg/ml tetracycline, 0.4% casamino acids and 1% glucose. When the growth attained KU 220, 3 β-indolylacrylic acid (IAA) was added to a concentration of 25 μg/ml, and then cultivation was continued for 4 hours. Thereafter, cells were harvested by centrifugation and suspended in a 1/10 volume of 0.05M Tris-HCl (pH 7.6) containing 10% sucrose. To this suspension, there were added phenylmethylsulfonyl fluoride, NaCl, ethylenediaminetetraacetate (EDTA), spermidine and lysozyme to concentrations of 1 mM, 0.2M, 10 mM, 40 mM and 200 μg/ml, respectively. The suspension was allowed to stand at 0° C. for 1 hour and then treated at 37° C. for 3 minutes. A lysate was obtained.

Centrifugation of this lysate at 4° C. and 20,000 rpm (Servall centrifuge, SS-34 rotor) for 30 minutes gave a supernatant containing the polypeptide (I) [X being a chemical bonding or/and Met, Y being Cys-Gln and Z being the peptide (III)]. When assayed, this supernatant showed an antiviral activity of $2.87 \times 10^8$ U/liter.

(ii) Cultivation of the transformant *E. coli* 294/pHITtrp 1201-d3 obtained in Example 1 (ii) in the same manner as Example 2 (i) followed by extraction gives a supernatant containing the peptide (I) [X being a chemical bonding or/and Met, Y being Gln or/and <Gln, and Z being the peptide (III)].

Measurement of the antiviral activity of this supernatant gives a value equivalent to that obtained in Example 2 (i).

(iii) Cultivation of the transformant *E. coli* 294/pHITtrp 1201-d4' obtained in Example 1 (iii) in the same manner as Example 2 (i) followed by extraction in the same manner gives a supernatant containing the polypeptide (I) [X being a chemical bonding or/and Met, Y being a chemical bonding and Z being the peptide (III)].

Measurement of the antiviral activity of this supernatant gives a value equivalent to that obtained in Example 2 (i).

(iv) Cultivation of the transformant *E. coli* 294/pHITtrp 1201-d4 obtained in Example 1 (iv) in the same manner as Example 2 (i) followed by extraction in the same manner gave a supernatant containing the polypeptide (I) [X being a chemical bonding or/and Met, Y being a chemical bonding and Z being the peptide (III)]. When assayed, this supernatant exhibited an antiviral activity of $2.5 \times 10^5$ U/liter.

EXAMPLE 3

Purification of polypeptide obtained by guanidine hydrochloride extraction (i) Frozen cells (5.9 g) obtained in the same manner as Example 2 (i) were suspended in 18 ml of 0.1M Trishydrochloric acid buffer (pH 7.0) containing 7M guanidine hydrochloride and 2 mM phenylmethylsulfonyl fluoride. After stirring at 4° C. for 1 hour, the suspension was centrifuged at 10,000×g for 30 minutes. The thus-obtained supernatant (20 ml) was diluted by addition of 260 ml of a buffer (pH 7.4) containing 137 mM sodium chloride, 2.7 mM potassium chloride, 8.1 mM disodium hydrogen phosphate and 1.5 mM monopotassium dihydrogen phosphate (hereinafter said buffer will be referred to as PBS) and the dilution was applied to an antibody column (Moγ2-11.1, column volume 12 ml) at a flow rate of 1 ml/minute. Thereafter, the column was washed with 60 ml of 20 mM sodium phosphate buffer (ph 7.0) containing 0.5M guanidine hydrochloride and then eluted with 36 ml of 20 mM sodium phosphate buffer (pH 7.0) containing 2M guanidine hydrochloride.

There was obtained 20 ml of a fraction having antiviral activity.

This fraction (20 ml) was applied to a column (2.6×94 cm, column volume 500 ml) of Sephacryl S-200 (Pharmacia equilibrated in advance with 25 mM ammonium acetate buffer (pH 6.0(containing 1 mM ethylenediaminetetraacetic acid, 0.15M sodium chloride, 10 mM cysteine and 2M guanidine hydrochloride, followed by elution with the same buffer. There was obtained 37 ml of an antivirally active fraction.

The polypeptide [I; X being a chemical bonding or-/and Met, Y being Cys-Gln and Z being the peptide (III)] obtained in this example weighed 5.9 mg and had a specific activity of $1.0 \times 10^7$ U/mg. In sodium dodecyl sulfate-polyacrylamide gel electrophoretic analysis of this sample according to Laemmli [Nature, 227, 680–685 (1970)], a protein band was detected at a location showing substantially the same mobility (molecular weight ca. 18,000) as that of mature type rIFN-γ [cf. U.S. patent application No. 534040 (filed Sept. 20, 1983)]. Electrophoresis under non-reducing conditions revealed a slight protein band at a location corresponding to the molecular weight of the dimer. Thus, the dimer formation was by far less as compared with the prior art rIFN-γ.

(ii) Frozen cells obtained by the procedure of Example 2 (ii) or (iii) are suspended in 3 volumes of 0.1 Trishydrochloric acid buffer (pH 7.0) containing 7M guanidine hydrochloride and 2 mM phenylmethylsulfonyl fluoride. The suspension is stirred at 4° C. for 1 hour and then centrifuged at 10,000×g for 30 minutes to give a clear and transparent supernatant. This supernatant is diluted 14-fold with PBS and applied to an antibody column (Moγ2-11.1). The column is washed with 20 mM sodium phosphate buffer (pH 7.0) containing 0.5M guanidine hydrochloride and then eluted with 20 mM sodium phosphate buffer (pH 7.0) containing 2M guanidine hydrochloride to give an antivirally active fraction. This fraction is applied to a column of Sephacryl S-200 (Pharmacia) equilibrated in advance with 25 mM mmonium acetate buffer (pH 6.0) containing 1 mM ethylenediaminetetraacetic acid, 0.15M sodium chloride, 10 mM cysteine and 2M guanidine hydrochloride and eluted with the same buffer to give an antivirally active fraction. The polypeptide (I) [X being a chemical bonding or/and Met, Y being Gln or/and <Gln and Z being the peptide (III)] or polypeptide (I) [X being a bond or/and Met, Y being a bond and Z being the peptide (III)] thus obtained each has a specific activity at least equivalent to that of the polypeptide (I) obtained in Example 3 (i).

EXAMPLE 4

Purification of polypeptide obtained by ultrasonic extraction

A 25-g portion of frozen cells obtained by the procedure of Example 2 (i), (ii) or (iii) are suspended in 1.5 volumes of 0.15M sodium borate buffer (pH 9.5). The suspension is stirred at 4° C. for 1 hour and then sonicated (30 seconds×5 times), followed by centrifugation at 30,000×g for 1 hour. The thus-obtained supernatant is mixed with 25 ml of silica gel washed in advance with PBS and the mixture is stirred gently at 4° C. for 1 hour. This silica gel mixture is then packed into a column, washed with 20–30 volumes (based on the column volume) of 1M NaCl and then eluted with 0.01M sodium borate buffer (pH 8.0) containing 0.5M tetramethylammonium chloride to give about 200 ml of an antivirally active fraction. This is divided into 4 subfractions, and each subfraction is applied to a monoclonal antibody (Moγ2-11.1) affinity column equilibrated with PBS. The column is washed with 10 volumes of PBS and then eluted with 20 mM sodium phosphate buffer (pH 7.0) containing 50% ethylene glycol and 1M sodium chloride. The antiviral activity is eluted with the first ca. 20-ml portion of the eluent. When each eluate containing the polypeptide (I) is subjected to SDS-polyacrylamide gel electrophoresis, bands corresponding to molecular weights of about 15,000 (15 Kd) and about 17,000 (17 Kd) are observed for each sample. In each case, the former is the major band.

What corresponds to the above 15 Kd is the polypeptide (I) [X being a chemical bonding or/and Met, Y being Cys-Gln and Z being Lys], polypeptide (I) [X being a chemical bonding or/and Met, Y being Gln or/and <Gln and Z being Lys] or polypeptide (I) [X being a chemical bonding or/and Met, Y being a chemical bonding and Z being Lys], respectively, whereas what corresponds to 17 Kd is the polypeptide (I) [X being a chemical bonding or/and Met, Y being Cys-Gln and Z being the peptide (II)], polypeptide (I) [X being a chemical bonding or/and Met, Y being Gln or/and <Gln and Z being the peptide (II)] or polypeptide (I) [X being a chemical bonding or/and Met, Y being a chemical bonding and Z being the peptide (II)], respectively.

EXAMPLE 5

Production of polypeptide (I) in which X is a bond or/and Met, Y is a bond and Z is the peptide (III)

(i) Using the expression plasmid pHITtrp1201-d4 constructed in Example 1 (iv), *Escherichia coli* C600 was transformed by the method of Cohen et al, (vide supra) to give a transformant, *Escherichia coli* C600/pHITtrp1201-d4, carrying the above plasmid.

(ii) *E. coli* C600/pHITtrp1201-d4 was inoculated into a 2-liter Erlenmeyer flask containing 500 ml of Luria medium (10.0 g Bacto-tryptone, 5.0 g yeast extract, 5.0 g NaCl, 1 liter distilled water) and seed culture was performed at 37±1° C. for 12 hours.

The culture obtained by the above seed culture was transferred to a 14-liter Chemapec glass fermenter containing 9.5 liters of Trp-8Mod3 medium [prepared by addding individually sterilized 30 g/liter glucose, 0.5 g/liter MgSO$_4$.7H$_2$O, 5 mg/liter thiamine hydrochloride, 0.1 g/liter sodium citrate, 50 mg/liter tryptophan and 5 mg/liter tetracycline to sterilized 5.0 g/liter (NH$_4$)$_2$HPO$_4$, 6.0 g/liter K$_2$HPO$_4$, 4.0 g/liter KH$_2$PO$_4$, 3.0 g/liter NaH$_2$PO$_4$.H$_2$O, 2.0 g/liter (NH$_4$)$_2$SO$_4$ and 0.7 ml antifoam (LB625)] and incubation was performed at 37° C. while adjusting the pH to 6.6–7.0 by adding 29% NH$_4$OH. After 13 hours, IAA was added.

Sampling was performed at timed intervals for measuring the bacterial growth and antiviral activity. The former was measured in terms of absorbance and the latter was determined with the supernatant obtained by centrifugation.

After 14 hours of incubation, the bacterial growth was maximal and the antiviral activity at that time was $5 \times 10^6$ U/liter.

INDUSTRIAL APPLICABILITY

The polypeptides (I) according to the invention have antiviral, antitumor and immunopotentiating activities, among others and are stable and therefore can advantageously be used as drugs, for instance.

We claim:

1. A polypeptide of the formula (N) H—X—Y—Asp Pro Tyr Val Lys Glu Ala Glu Asn
Leu Lys Lys Tyr Phe Asn Ala Gly His Ser Asp Val
Ala Asp Asn Gly Thr Leu Phe Leu Gly Ile Leu Lys
Asn Trp Lys Glu Glu Ser Asp Arg Lys Ile Met Gln
Ser Gln Ile Val Ser Phe Tyr Phe Lys Leu Phe Lys
Asn Phe Lys Asp Asp Gln Ser Ile Gln Lys Ser Val -continued Glu Thr Ile Lys Glu Asp Met Asn Val Lys Phe Phe
Asn Ser Asn Lys Lys Arg Asp Asp Phe Glu Lys
Leu Thr Asn Tyr Ser Val Thr Asp Leu Asn Val Gln
Arg Lys Ala Ile His Glu Leu Ile Gln Val Met Ala
Glu Leu Ser Pro Ala Ala Lys Thr Gly—Z—OH (C)

wherein X is Met or a bond, Y is Cys-Gln, Gln, <Gln or a bond and Z is a peptide or amino acid residue having 1 to 16 amino acids counting from the N terminus of the peptide chain of (N) Lys Arg Lys Arg Ser Gln Met Leu Phe Arg Gly Arg Arg Ala Ser Gln (C).

* * * * *